(12) United States Patent
Nomura et al.

(10) Patent No.: US 7,750,159 B2
(45) Date of Patent: Jul. 6, 2010

(54) PHENANTHROLINE DERIVATIVE AND LIGHT EMITTING ELEMENT AND LIGHT EMITTING DEVICE USING THE SAME

(75) Inventors: Ryoji Nomura, Kanagawa (JP); Daisuke Kumaki, Nigata (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 148 days.

(21) Appl. No.: 10/579,114

(22) PCT Filed: Jun. 29, 2005

(86) PCT No.: PCT/JP2005/012436

§ 371 (c)(1),
(2), (4) Date: May 11, 2006

(87) PCT Pub. No.: WO2006/004138

PCT Pub. Date: Jan. 12, 2006

(65) Prior Publication Data

US 2007/0145353 A1     Jun. 28, 2007

(30) Foreign Application Priority Data

Jul. 7, 2004  (JP) ............................. 2004-200059

(51) Int. Cl.
*C07D 471/02* (2006.01)
*H01L 51/50* (2006.01)

(52) U.S. Cl. ................. 546/49; 428/690; 428/917; 313/506

(58) Field of Classification Search ............. 546/49; 428/917, 690; 313/506
See application file for complete search history.

(56) References Cited

U.S. PATENT DOCUMENTS

| | | | |
|---|---|---|---|
| 5,393,614 A | 2/1995 | Nakada | 428/690 |
| 2004/0265626 A1 | 12/2004 | Shibanuma et al. | 428/690 |

FOREIGN PATENT DOCUMENTS

| | | |
|---|---|---|
| EP | 0 564 224 | 10/1993 |
| EP | 1 097 980 | 5/2001 |
| JP | 05-331459 | 12/1993 |
| JP | 2001-131174 | 5/2001 |
| JP | 2003-017268 | 1/2003 |
| JP | 2004-107263 | 4/2004 |
| JP | 2004-175691 | 6/2004 |
| JP | 2005-108720 | 4/2005 |
| WO | WO 2004/026870 | 4/2004 |

OTHER PUBLICATIONS

International Search Report re application No. PCT/JP2005/012436, dated Aug. 30, 2005.
Written Opinion re application No. PCT/JP2005/012436, dated Aug. 30, 2005.

*Primary Examiner*—Charanjit S Aulakh
(74) *Attorney, Agent, or Firm*—Husch Blackwell Sanders LLP

(57) ABSTRACT

It is an object of the present invention to provide a novel material that can be used for an electron injecting material. In addition, it is an object of the present invention to provide a light-emitting element that is able to broaden choices for an electrode material.

An aspect of the present invention is an electron injecting material represented by a general formula (2). In the general formula (2), $R_6$ is selected from the group consisting of an alkyl group having 1 to 4 carbon atoms, an alkenyl group having 1 to 4 carbon atoms, and an aryl group having 6 to 10 carbon atoms, where the alkenyl group and the aryl group may have a substituent.

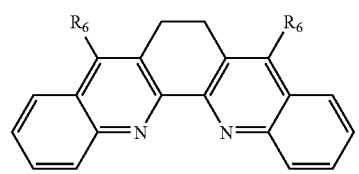

(2)

10 Claims, 12 Drawing Sheets

PHENANTHROLINE DERIVATIVE AND LIGHT EMITTING ELEMENT AND LIGHT EMITTING DEVICE USING THE SAME

TECHNICAL FIELD

The present invention relates to a phenanthroline derivative that can be used for an electron injecting material, and related to a light-emitting element using the phenanthroline derivative and a light-emitting device using the phenanthroline derivative.

BACKGROUND ART

These days, many of light-emitting elements that are used for displays and the like have a structure in which a layer including a luminescent material is interposed between a pair of electrodes. In the case of such a light-emitting element, light is emitted when an exciton formed by recombination of an electron injected from one electrode and a hole injected from the other returns to the ground state.

In the field of light-emitting elements, various studies have been conducted in order to obtain a light-emitting element that has favorable characteristics such as a high luminous efficiency.

For example, in Patent Reference 1, an organic electroluminescent element using a phenanthroline derivative is disclosed. In the element described in Patent Document 1, the phenanthroline derivative is used for an electron transporting layer.

However, in the case of the element described in Patent Document 1, while favorable characteristics can be obtained when an Mg—Ag alloy is used for an electrode as in embodiments, there is a possibility that electrons are not well injected into an electron transporting layer to make the driving voltage larger when an electrode composed of aluminum is used.

(Patent Reference 1) Japanese Patent Application Laid-Open No. 5-331459

DISCLOSURE OF INVENTION

It is an object of the present invention to provide a novel material that can be used for an electron injecting material. In addition, it is an object of the present invention to provide a light-emitting element that is able to broaden choices for an electrode material.

An aspect of the present invention is a phenanthroline derivative represented by a general formula (1).

(1)

In the general formula (1), each of $R_1$ to $R_5$ is selected from the group consisting of a hydrogen atom, an alkyl group having 1 to 4 carbon atoms and a halogen group.

Another aspect of the present invention is an electron injecting material represented by a general formula (2).

(2)

In the general formula (2), $R_6$ is selected from the group consisting of an alkyl group having 1 to 4 carbon atoms, an alkenyl group having 1 to 4 carbon atoms, and an aryl group having 6 to 10 carbon atoms, where the alkenyl group and the aryl group may have a substituent.

Another aspect of the present invention is a light-emitting element that has a layer including a phenanthroline derivative represented by a general formula (3) and at least one element selected from alkali metals and alkali-earth metals.

(3)

In the general formula (3), $R_7$ is selected from the group consisting of an alkyl group having 1 to 4 carbon atoms, an alkenyl group having 1 to 4 carbon atoms, and an aryl group having 6 to 10 carbon atoms, where the alkenyl group and the aryl group may have a substituent.

Another aspect of the present invention is a light-emitting element that has a layer including a phenanthroline derivative represented by the general formula (3) and at least one element selected from alkali metals and alkali-earth metals between pair of electrodes.

According to the present invention, a novel material that can be used for an electron injecting material can be obtained, and thus, material choices are broadened. In addition, according to the present invention, an electron injecting material that is capable of injecting electrons well can be obtained by using the novel material in combination with an alkali metal or an alkali-earth metal.

Further, according to the present invention, an electrode to serve as a cathode can be formed with the use of a material that has a high work function, and thus, a light-emitting element that is able to broaden choices for an electrode material can be obtained. In addition, according to the present invention, a light-emitting device that is driven with low power consumption can be obtained.

BEST MODE FOR CARRYING OUT THE INVENTION

Embodiment modes of the present invention will be described below. However, the present invention may be embodied in a lot of different forms, and it is to be easily understood that various changes and modifications will be apparent to those skilled in the art unless such changes and modifications depart from the scope of the present invention. Therefore, the present invention is not to be construed with limitation to what is described in the embodiment modes.

Embodiment Mode 1

Aspects of phenanthroline derivatives according to the present invention are represented by structure formulas (4) to (7).

(4)

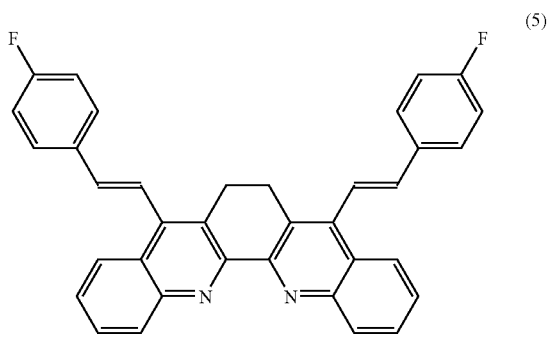

(5)

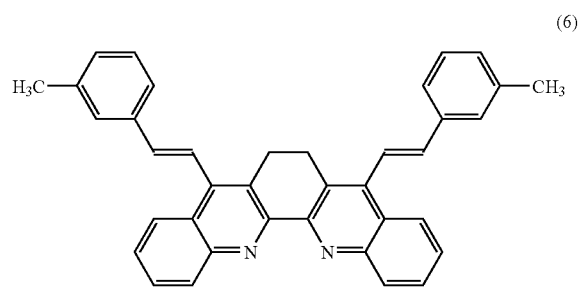

(6)

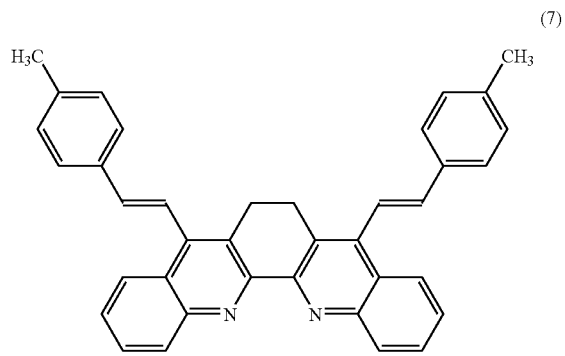

(7)

The phenanthroline derivatives represented by the structure formulas (4) to (7) can be synthesized in accordance with a synthesis scheme (a-1).

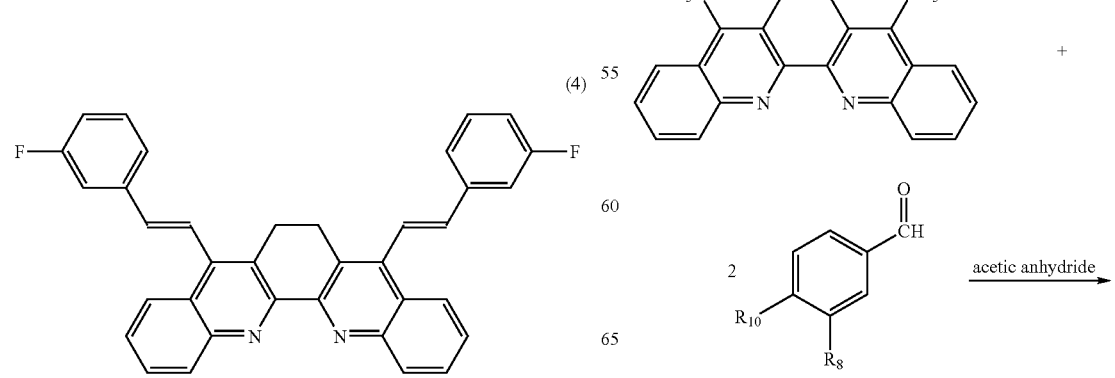

-continued

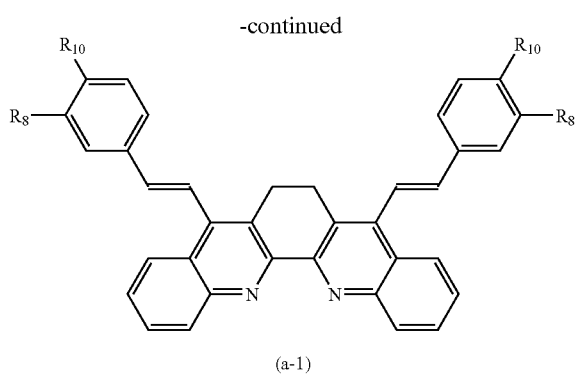

(a-1)

In the synthesis scheme (a-1), each of $R_8$ and $R_{10}$ is selected from the group consisting of a hydrogen atom, an alkyl group having 1 to 4 carbon atoms and a halogen group.

The phenanthroline derivatives in the present embodiment can be used as an electron injecting material for forming an electron injecting layer. In addition, the present invention broadens choices for a material to be used for forming an electron injecting layer.

Embodiment Mode 2

An embodiment mode of a light-emitting element according to the preset invention will be described with reference to FIG. 1.

Figure 1:
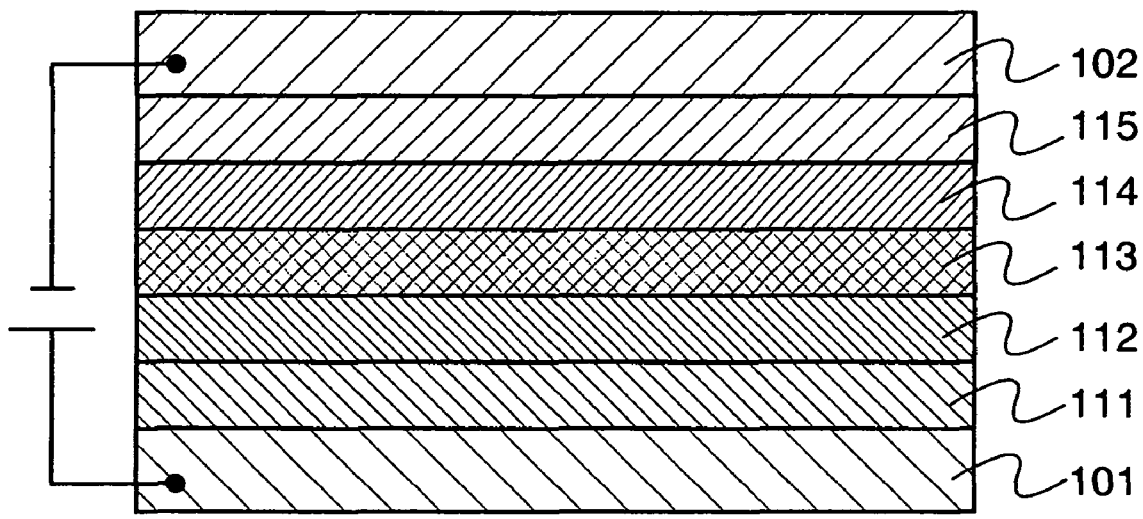
FIG. 1 is a diagram illustrating the structure of a light-emitting element according to the present invention.

FIG. 1 is a diagram illustrating a light-emitting element that has a light-emitting layer 113 between a first electrode 101 and a second electrode 102.

In this light-emitting element, a hole emitted from the first electrode 101 and an electron injected from the second electrode 102 are recombined in the light-emitting layer 113 to bring a luminescent material to an excited state. Then, light is emitted when the luminescent material in the excited state returns to the ground state. It is to be noted that the first electrode 101 and the second electrode 102 respectively serve as an anode and a cathode in the light-emitting element in the present embodiment, and that the luminescent material is a material that is capable of producing luminescence of a desired emission wavelength with a favorable luminous efficiency.

Here, the light-emitting layer 113 is not particularly limited. However, it is preferable that the light-emitting layer 113 be a layer in which the luminescent material is included so as to be dispersed in a layer composed of a material that has a larger energy gap than the luminescent material. This makes it possible to prevent quenching of luminescence from the luminescent material due to the concentration of the luminescent material itself. It is to be noted that an energy gap indicates an energy gap between a LUMO level and a HOMO level.

The luminescent material is not particularly limited, for which a material that is excellent in luminous efficiency and is capable of producing luminescence of a desired emission wavelength may be used. For example, when red or reddish luminescence is desired to be obtained, a material that produces luminescence with an emission spectrum peak from 600 nm to 680 nm, such as 4-dicyanomethylene-2-isopropyl-6-[2-(1,1,1,1~tetramethyl-9-julolidyl)-ethenyl]-4H-pyran (abbreviation: DCJTI), 4-dicyanomethylene-2-methyl-6-[2-(1,1,7,7-tetramethyl-9-julolidyl)-ethenyl]-4H-pyran (abbreviation: DCJT), 4-dicyanomethylene-2-tert-butyl-6-[2-(1,1,7,7-tetramethyl-9-julolidyl)-ethenyl]-4H-pyran (abbreviation: DCJTB), periflanthene, or 2,5-dicyano-1,4-bis-[2-(10-methoxy-1,1,7,7-tetramethyl-9-julolidyl)-ethenyl]-benzene, can be used. When green or greenish luminescence is desired to be obtained, a material that produces luminescence with an emission spectrum peak from 500 nm to 550 nm, such as N,N'-dimethylquinacridone (abbreviation: DMQd), coumarin 6, coumarin 545T, or tris(8-quinolinolato) aluminum (abbreviation: $Alq_3$), can be used. When blue- or bluish luminescence is desired to be obtained, a material that produces luminescence with an emission spectrum peak from 420 nm to 500 nm, such as 9,10-di(2-naphthyl)-2-tert-butylanthracene (abbreviation: t-BuDNA), 9,9'-bianthryl, 9,10-diphenylanthracene (abbreviation: DPA), 9,10-di(2-naphthyl) anthracene (abbreviation: DNA), bis(2-methyl-8-quinolinolato)-4-phenylphenolato-gallium (abbreviation: BGaq), or bis(2-methyl-8-quinolinolato)-4-phenylphenolato-aluminum (abbreviation: BAlq), can be used.

The material to be used for dispersing the luminescent material is not particularly limited. In addition to anthracene derivatives such as 9,10-di(2-naphthyl)-2-tert-butylanthracene (abbreviation: t-BuDNA) and carbazole derivatives such as 4,4'-bis(N-carbazolyl)-biphenyl (abbreviation: CBP), metal complexes such as bis[2-(2'-hydroxyphenyl)-pyridinato]zinc (abbreviation: $Znpp_2$) and bis[2-(2'-hydroxyphenyl)-benzoxazolato]zinc (abbreviation: ZnBOX) can be used.

Although the first electrode 101 is not particularly limited, it is preferable that the first electrode 101 is formed by using a material that has a larger work function when the first electrode 101 functions as an anode as in the present embodiment mode. Specifically, in addition to indium tin oxide (ITO), indium tin oxide including silicon oxide, and indium oxide including zinc oxide at 2 to 20%, gold (Au), platinum (Pt), nickel (Ni), tungsten (W), chromium (Cr), molybdenum (Mo), iron (Fe), cobalt (Co), copper (Cu), palladium (Pd), and the like can be used. The first electrode 101 can be formed by, for example, sputtering or evaporation.

In addition, although the second electrode 102 is not particularly limited, it is preferable that the second electrode 102 is formed by using a material that has a smaller work function when the second electrode 102 functions as a cathode as in the present embodiment mode. Specifically, it is preferable to use aluminum or the like, and an alkali metal or an alkali-earth metal such as lithium (Li) or magnesium may be included in aluminum. The second electrode 102 can be formed by, for example, sputtering or evaporation.

Further, in order to extract emitted light to the outside, it is preferable that any one or both of the first electrode 101 and the second electrode 102 be an electrode composed of a material such as indium tin oxide or an electrode formed to be several to several tens nm in thickness so that visible light can be transmitted.

In addition, a hole transporting layer 112 is provided between the first electrode 101 and the light-emitting layer 113 as shown in FIG. 1. Here, a hole transporting layer is a layer that has a function of transporting holes injected from the first electrode 101 to the light-emitting layer 113. By providing the hole transporting layer 112 to keep the first electrode 101 away from the light-emitting element 113 in this way, quenching of emission due to a metal can be prevented.

The hole transporting layer 112 is not particularly limited, and it is possible to use a layer formed with the use of, for example, an aromatic amine compound (that is, compound including a bond of a benzene ring-nitrogen) such as 4,4'-bis[N-(I-naphthyl)-N-phenyl-amino]-biphenyl (abbreviation: α-NPD), 4,4'-bis[N-(3-methylphenyl)-N-phenyl-amino]-biphenyl (abbreviation: TPD), 4,4',4"-tris(N,N-diphenyl-amino)-triphenylamine (abbreviation: TDATA), or 4,4',4"-tris[N-(3-methylphenyl)-N-phenyl-amino]-triphenylamine (abbreviation: MTDATA).

In addition, the hole transporting layer 112 may be a layer that has a multilayer structure formed by combining two or more layers each including the material mentioned above.

Further, an electron transporting layer 114 may be provided between the second electrode 102 and the light-emitting layer 113 as shown in FIG. 1. Here, an electron transporting layer is a layer that has a function of transporting electrons injected from the second electrode 102 to the light-emitting layer 113. By providing the electron transporting layer 114 to keep the second electrode 102 away from the light-emitting element 113 in this way, quenching of emission due to a metal can be prevented.

The electron transporting layer 114 is not particularly limited, and it is possible to use a layer formed with the use of, for example, a metal complex including a quinoline skeleton or a benzoquinoline skeleton such as tris(8-quinolinolato) aluminum (abbreviation: Alq3), tris(4-methyl-8-quinolinolato) aluminum (abbreviation: Almq$_3$), bis(10-hydroxybenzo[h]quinolinato) beryllium (abbreviation: BeBq$_2$), or bis(2-methyl-8-quinolinolato)-4-phenylphenolato-aluminum (abbreviation: BAlq). In addition, a layer formed with the use of, for example, a metal complex including a oxazole ligand or a thiazole-based ligand such as bis[2-(T-hydroxyphenyl)-benzoxazolato]zinc (abbreviation: ZnBOX) or bis[2-(2'-hydroxyphenyl)-benzothiazolato]zinc (abbreviation: Zn(BTZ)$_2$), may be used. Further, a layer formed with the use of 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: to as OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP) or the like may be used. It is preferable to form the electron transporting layer 114 with the use of a material in which the mobility of an electron is higher than that of a hole as described above. Further, it is more preferable to form the electron transporting layer 114 with the use of a material that has an electron mobility of $10^{-6}$ cm$^2$/Vs or more. In addition, the electron transporting layer 114 may be a layer that has a multilayer structure formed by combining two or more layers each including the material mentioned above.

Further, a hole injecting layer may be provided between the first electrode 101 and the hole transporting layer 112 as shown in FIG. 1. Here, a hole injecting layer is a layer that has a function of assisting injection of holes from an electrode to serve as an anode to the hole transporting layer 112.

The hole injecting layer 111 is not particularly limited, and it is possible to use a layer formed with the use of, for example, a metal oxide such as molybdenum oxide (MoOx), vanadium oxide (VOx), ruthenium oxide (RuOx), tungsten oxide (WOx), manganese oxide (MnOx). In addition, the hole injecting layer 111 Can be formed with the use of a phthalocyanine compound such as phthalocyanine (abbreviation: H$_2$Pc), copper phthalocyanine (abbreviation: CuPc), an aromatic amine compound such as 4,4'-bis[N-{4-(N,N-di-m-tolylamino) phenyl}-N-phenylamino]biphenyl (abbreviation: DNTPD), or a polymer such as poly(ethylenedioxythiophene)/poly(styrene sulfonate) aqueous solution (PEDOT/PSS).

Further, an electron injecting layer 115 may be provided between the second electrode 102 and the electron transporting layer 114 as shown in FIG. 1. Here, an electron injecting layer is a layer that has a function of assisting injection of electrons from an electrode to serve as a cathode to the electron transporting layer 114. It is to be noted that injection of electrons into a light-emitting layer may be assisted by providing an electron injecting layer between an electrode to serve as a cathode and the light-emitting layer when no electron transporting layer is particularly provided.

The electron injecting layer 115 is a layer including a phenanthroline derivative according to the present invention. Although the electron injecting layer 115 is not particularly limited, it is preferable that the electron injecting layer 115 be a layer including a phenanthroline derivative represented by the following general formula (8) and one of an alkali metal such as lithium and an alkali-earth metal such as magnesium. In addition, among phenanthroline derivatives represented by the general formula (8), it is more preferable to be a phenanthroline derivative represented by any one of the following structure formulas (4) to (7), (9), and (10). By using the phenanthroline derivative represented by the general formula (8) as an electron injecting material for forming the electron injecting layer 115 as described above, a light-emitting element that is driven well can be obtained even when the second electrode 102 is formed with the use of a material that has a larger work function. Therefore, for example, it is also easier to use indium tin oxide as an electrode material, and choices for an electrode material are thus broaden. In addition, by using the phenanthroline derivative represented by the general formula (8) as an electron injecting material for forming the electron injecting layer 115, a light-emitting element that is driven well can be obtained even when the second electrode 102 is formed with the use of not an expensive material such as silver including magnesium or aluminum including lithium but an inexpensive material such as aluminum.

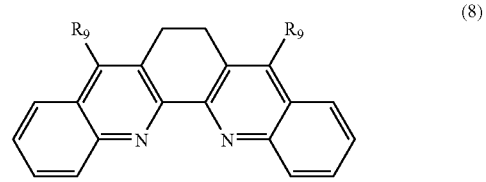

(8)

In the general formula (8), R$_9$ is selected from the group consisting of an alkyl group having 1 to 4 carbon atoms, an alkenyl group having 1 to 4 carbon atoms, and an aryl group having 6 to 10 carbon atoms, where the alkenyl group and the aryl group may have a substituent.

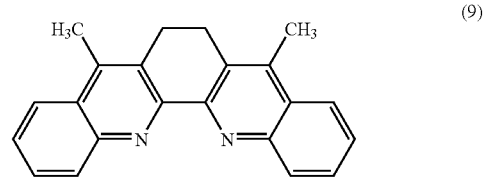

(9)

-continued

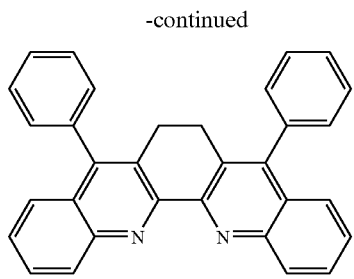

(10)

In the above-described light-emitting element according to the present invention, each of the hole injecting layer 111, the hole transporting layer 112, the light-emitting layer 113, the electron transporting layer 114, and the electron injecting layer 115 may be formed by any one method of evaporation, inkjet, and coating. In addition, the first electrode 101 and the second electrode 102 may be formed by any one method of sputtering and evaporation.

The above-described light-emitting element according to the present invention is capable of performing electron injection efficiently. Therefore, the light-emitting element according to the present invention is driven at a low driving voltage. In addition, since the light-emitting element according to the present invention has a wide range of choice for an electron material, the electrode can be formed with the use of an inexpensive material. Therefore, the light-emitting element according to the present invention can be manufactured at low cost.

Embodiment Mode 3

The light-emitting element according to the present invention, which is described in Embodiment mode 2, can perform electron injection efficiently and is driven at a low driving voltage. Therefore, a light-emitting device that is driven with low power consumption can be obtained by applying the light-emitting element according to the present invention to a pixel portion or the like. In addition, since the light-emitting element according to the present invention can be manufactured at low cost, an inexpensive light-emitting device can be manufactured by applying the light-emitting element according to the present invention to a pixel portion or the like.

In the present embodiment mode, a circuit configuration and driving method of a light-emitting device that has a display function will be described with reference to FIGS. 3 to 6.

Figure 3:
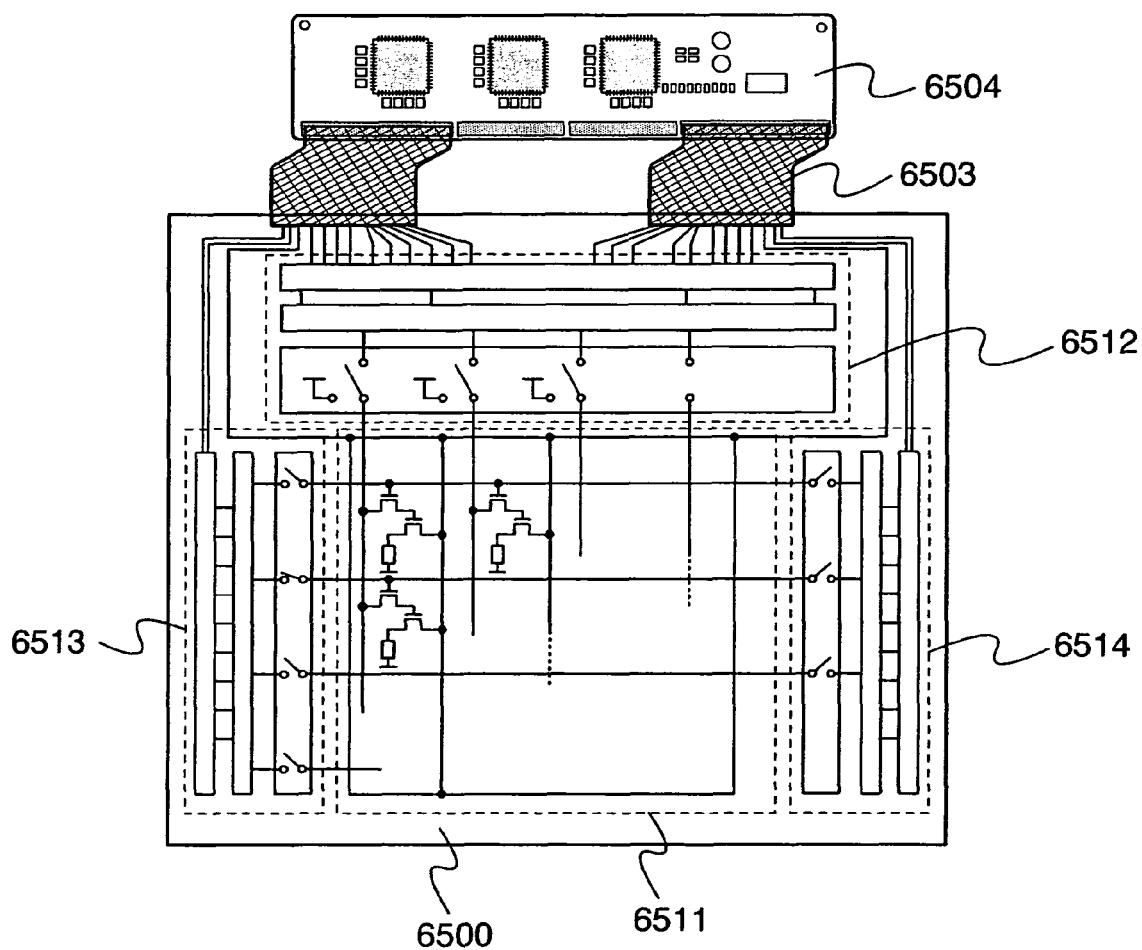
FIG. 3 is a diagram illustrating a light-emitting device to which the present invention is applied.

FIG. 3 is a top schematic view of a light-emitting device to which the present invention is applied. In FIG. 3, a pixel portion 6511, a source signal line driver circuit 6512, a writing gate signal line driver circuit 6513, and an erasing gate signal line driver circuit 6514 are provided over a substrate 6500. Each of the source signal line driver circuit 6512, the writing gate signal line driver circuit 6513, and the erasing gate signal line driver circuit 6514 is connected to FPC (Flexible Printed Circuit) 6503 that is an external input terminal through a group of wirings. Further, each of the source signal line driver circuit 6512, the wiring gate signal line driver circuit 6513, and the erasing gate signal line driver circuit 6514 receives signals such as a video signal, a clock signal, a start signal, and a reset signal from the FPC 6503. In addition, a printed wiring board (PWB) 6504 is attached to the FPC 6503. It is to be noted that it is not always necessary to provide the driver circuit portion on the same substrate on which the pixel portion 6511 is provided as described above. For example, the driver circuit portion may be provided outside the substrate by using a TCP that has an IC chip on an FPC on which a wiring pattern is formed.

In the pixel portion 6511, a plurality of source signal lines extending in a column direction is arranged in a row direction, current supply lines are arranged to line in a row direction, and a plurality of gate signal lines extending in a row direction is arranged to line in a column direction. Further, in the pixel portion 6511, a plurality of circuits each including a light-emitting element is arranged.

Figure 4:
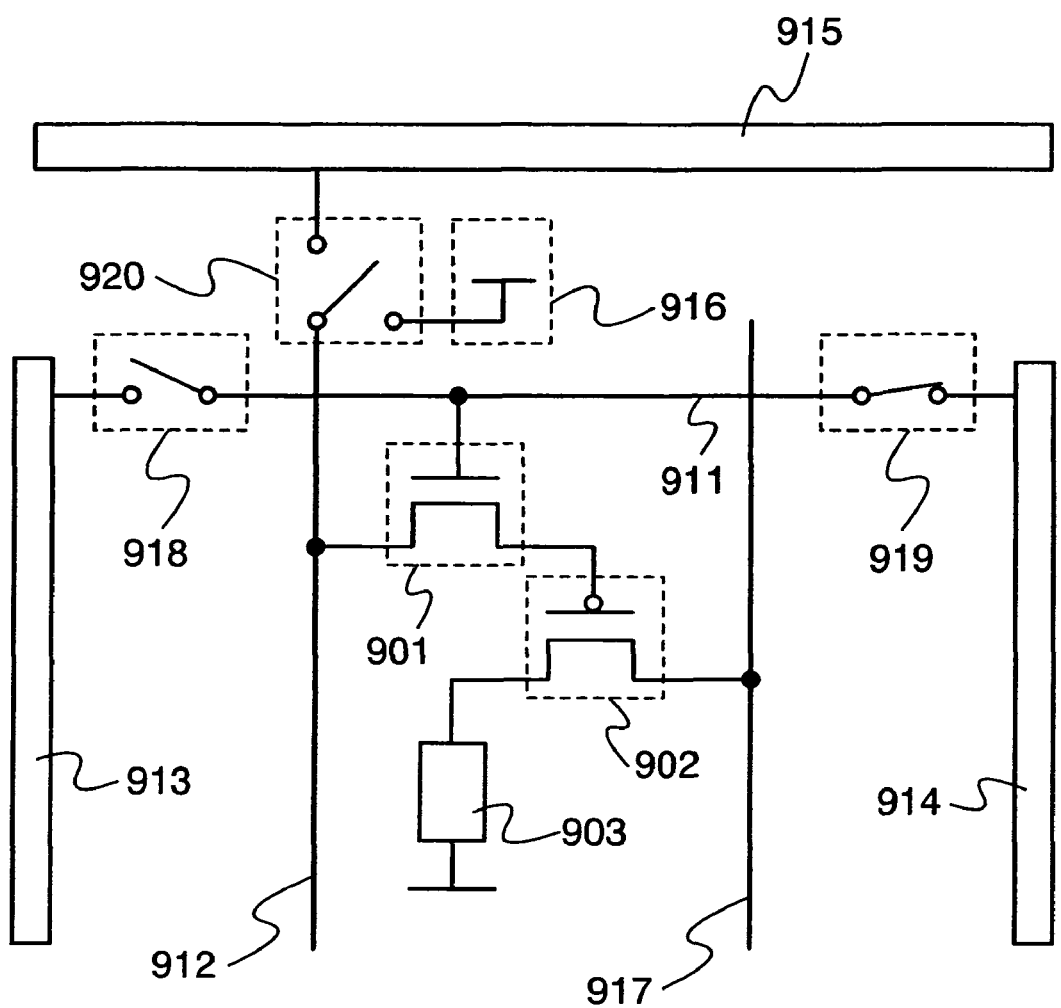
FIG. 4 is a diagram illustrating a circuit included in a light-emitting device to which the present invention is applied.

FIG. 4 is a diagram showing a circuit for operating one pixel. The circuit shown in FIG. 4 includes a first transistor 901, a second transistor 902, and a light-emitting element 903.

Each of the first transistor 901 and the second transistor 902 is a three-terminal element including a gate electrode, a drain region, and a source region, and including a channel region between the drain region and the source region. Here, since a source region and a drain region are switched with each other in accordance with a structure or operating conditions of a transistor, it is difficult to identify which one is the drain region or the source region. Consequently, regions that serve as a source or a drain are referred to as first and second electrodes of a transistor in the present embodiment mode.

A gate signal line 911 and a writing gate signal line driver circuit 913 are provided so as to be electrically connected or unconnected by a switch 918, the gate signal line 911 and an erasing gate signal line driver circuit 914 are provided so as to be electrically connected or unconnected by a switch 919, and a source signal line 912 is provided so as to be electrically connected to any one of a source signal line driver circuit 915 and a power source 916 by a switch 920. Further, the first transistor 901 has a gate electrically connected to the gate signal line 911, a first electrode electrically connected to the source signal line 912, and a second electrode electrically connected to a gate electrode of the second transistor 902. The second transistor 902 has a first electrode electrically connected to a current supply line 917 and a second electrode electrically connected to one electrode included in the light-emitting element 903. It is to be noted that the switch 918 may be included in the writing gate signal line driver circuit 913, the switch 919 may be included in the erasing gate signal line driver circuit 914, and the switch 920 may be included in the source signal line driver circuit 915.

Figure 5:
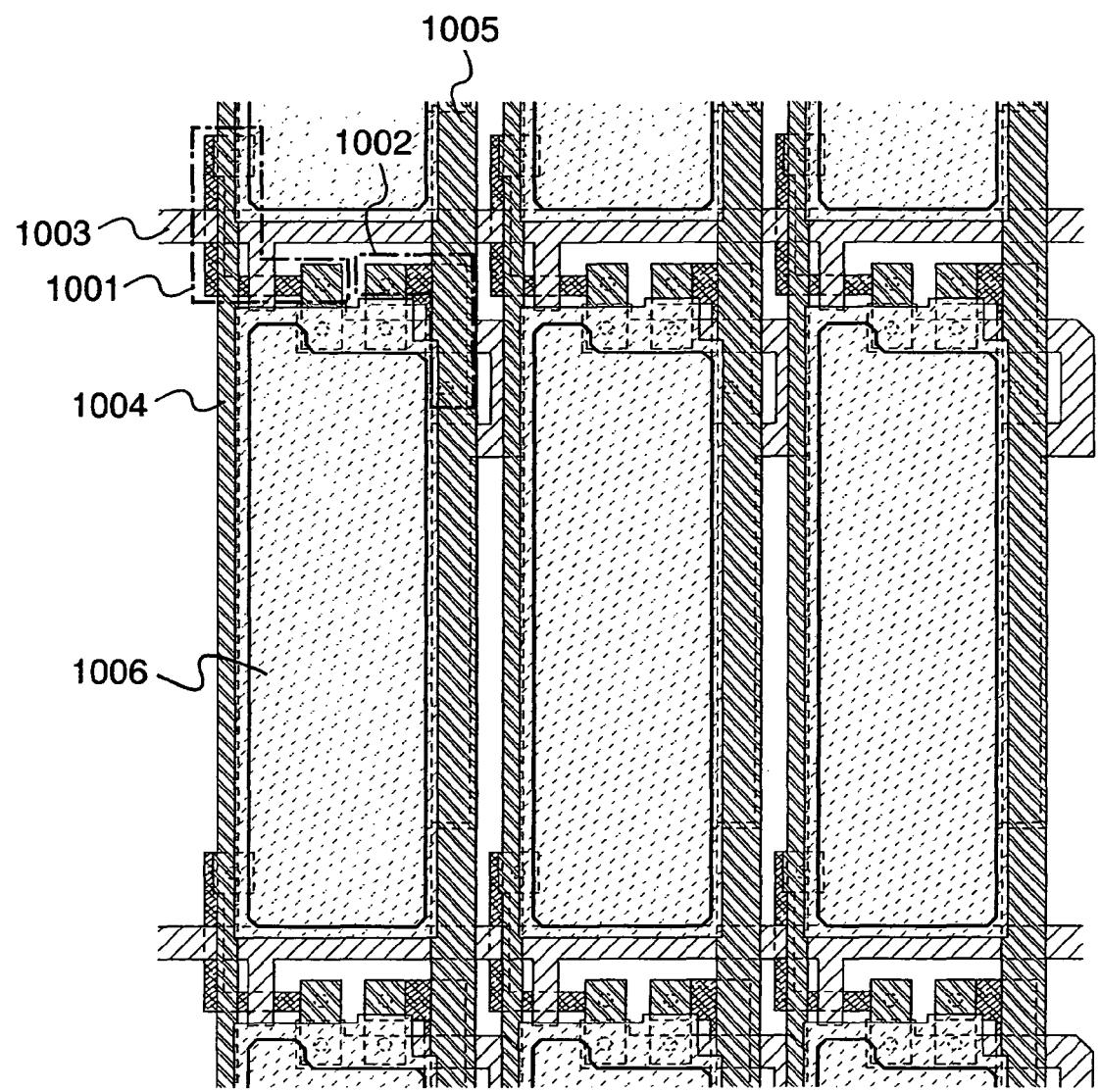
FIG. 5 is a top view of a light-emitting device to which the present invention is applied.

In addition, arrangement of a transistor, a light-emitting element, and the like is not particularly limited. For example, arrangement shown in a top view of FIG. 5 can be employed. In FIG. 5, a first transistor 1001 has a first electrode connected to a source signal line 1004 and a second electrode connected to a gate electrode of a second transistor 1002. Further, the second transistor 1002 has a first electrode connected to a current supply line 1005 and a second electrode connected an electrode 1006 of a light-emitting element. A portion of a gate signal line 1003 serves as a gate electrode of the first transistor 1001.

Figure 6:
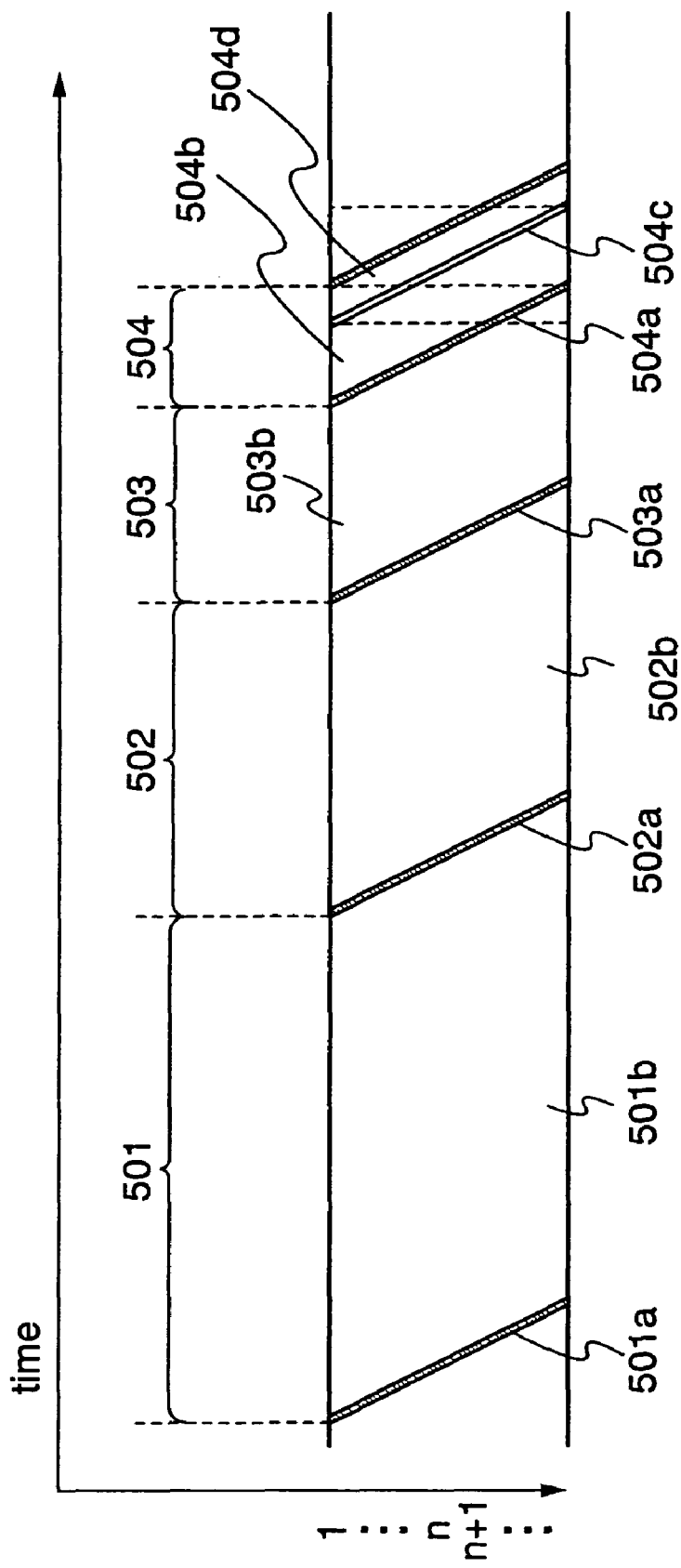
FIG. 6 is a diagram illustrating operation per frame for a light-emitting device to which the present invention is applied.

Next, a driving method will be described. FIG. 6 is a diagram illustrating operation per frame with time. In FIG. 6, the lateral direction indicates passage of time, and the vertical direction indicates ordinal numbers of gate signal lines.

When a light-emitting device according to the present invention is used to display images, rewrite operation and image display operation for a screen are repeated in a display period. Although the number of rewrites is not particularly limited, it is preferable that the number of rewrites be about 60 times per second so as not to make an image viewer recognize flickers. Here, a period for which rewrite operation and display operation are performed for a screen (one frame) is referred to as one frame period.

As shown in FIG. 6, one frame is divided into four sub-frames 501, 502, 503, and 504 respectively including writing periods 501a, 502a, 503a, and 504a and retention periods 501b, 502b, 503b, and 504b. In the retention period, a light-emitting element to which a signal for emitting light is given is made to be in an emitting state. The ratio of the length of the retention period in each sub-frame is first sub-frame 501 second sub-frame 502: third sub-frame 503: fourth sub-frame 504=$2^3:2^2:2^1:2^0$=8:4:2:1. This makes 4-bit gradation possible. However, the number of bits or the number of gradations is not limited to that described here. For example, eight sub-frames may be provided so as to perform 8-bit gradation.

Operation in one frame will be described. First, in the sub-frame 501, writing operation is sequentially performed for each of the first row to the last row. Accordingly, the start time of the writing period 501a is different depending on the row. When the writing period 501a is completed, the row is sequentially moved into the retention period 501b. In the retention period 501b, a light-emitting element to which a signal for emitting light is given is made to be in an emitting state. Further, when the retention period 501b is completed, the row is sequentially moved into the next sub-frame 502, and writing operation is sequentially performed for each of the first row to the last row as in the case of the sub-frame 501. The operation described above is repeated to complete the retention period 504b of the sub-frame 504. When the operation in the sub-frame 504 is completed, the row is moved into the next frame. Thus, the total of time for which light is emitted in each sub-frame is emission time for each light-emitting element in one frame. By varying this emission time with respect to each light-emitting element to have various combinations in one pixel, various different display colors in luminosity and chromaticity can be made.

As in the sub-frame 504, when forcible termination of a retention period of a row for which writing is already completed to move into the retention time is required before writing for the last row is completed, it is preferable that an erasing period 504c be provided after the retention period 504b and a row be controlled so as to be in a non-emitting state forcibly. Further, the row made to be in the non-emitting state forcibly is kept the non-emitting state for a certain period (this period is referred to as a non-emission period 504d). Then, immediately after the writing period 504a of the last row is completed, the rows are sequentially moved into the next writing period (or the next frame), starting from the first row. This makes it possible to prevent the writing period 504a of the sub-frame 504 from overlapping with the writing period of the next sub-frame.

Although the sub-frames 501 to 504 are arranged in the order of retention period from longest to shortest in the present embodiment, the arrangement as in the present embodiment mode is not always necessary. For example, the sub-frames 501 to 504 may be arranged in the order of retention period from shortest to longest, or may be arranged in random order. In addition, the sub-frames may be divided further into a plurality of frames. Namely, scanning of the gate signal lines may be performed more than once while giving the same image signal.

Now, operation of the circuit shown in FIG. 4 in a writing period and an erasing period will be described.

First, operation in a writing period will be described. In the writing period, the n-th (n is a natural number) gate signal line 911 is electrically connected to the writing gate signal line driver circuit 913 through the switch 918, and unconnected to the erasing gate signal line driver circuit 914. In addition, the source signal line 912 is electrically connected to the source signal line driver circuit 915 through the switch 920. In this case, a signal is input to the gate of the first transistor 901 connected to the n-th (n is a natural number) gate signal line 911 to turn on the first transistor 901. Then, at this moment, image signals are input simultaneously to the first to last source signal lines 912. It is to be noted that the image signals input from the respective source signal lines 912 are independent of each other. The image signal input from each of the source signal lines 912 is input to the gate electrode of the second transistor 902 through the first transistor 901 connected to the source signal line 912. At this moment, the value of current to be supplied from the current supply line 917 to the light-emitting element 903 is determined in accordance with the signal input to the second transistor 902. Then, depending on the value of the current, whether the light-emitting element 903 emits light or not is determined. For example, when the second transistor 902 is a p-channel transistor, the light-emitting element 903 is made to emit light by inputting a Low Level signal to the gate electrode of the second transistor 902. On the other hand, when the second transistor 902 is an n-channel transistor, the light-emitting element 903 is made to emit light by inputting a High Level signal to the gate electrode of the second transistor 902.

Next, operation in an erasing period will be described. In the erasing period, the n-th (n is a natural number) gate signal line 911 is electrically connected to the erasing gate signal line driver circuit 914 through the switch 919. In addition, the source signal line 912 is electrically connected to the power source 916 through the switch 920. In this case, a signal is input to the gate of the first transistor 901 connected to the n-th (n is a natural number) gate signal line 911 to turn on the first transistor 901. Then, at this moment, erasing signals are input simultaneously to the first to last source signal lines 912. The erasing signal input from each of the source signal lines 912 is input to the gate electrode of the second transistor 902 through the first transistor 901 connected to the source signal line 912. At this moment, current supply from the current supply line 917 to the light-emitting element 903 is stopped in accordance with the signal input to the second transistor 902. Then, the light-emitting element 903 is forcibly made to be in a non-emitting state. For example, when the second transistor 902 is a p-channel transistor, the light-emitting element 903 is made to emit no light by inputting a High Level signal to the gate electrode of the second transistor 902. On the other hand, when the second transistor 902 is an n-channel transistor, the light-emitting element 903 is made to emit no light by inputting a Low Level signal to the gate electrode of the second transistor 902.

It is to be noted that, as for the n-th row (n is a natural number), signals for erasing are input by the operation as described above in an erasing period. However, as described above, the other row (referred to as the m-th row (m is a natural number)) may be in a writing period while the n-th row is in an erasing period. In such a case, it is necessary to input a signal for erasing to the n-th row and input a signal for writing to the m-th row by using the same source signal line. Therefore, operation described below is preferable.

Immediately after the n-th light-emitting element 903 is made to emit no light by the operation in the erasing period described above, the gate signal line 911 and the erasing gate signal line driver circuit 914 are made to be unconnected to each other, and the switch 920 is switched to connect the source signal line 912 and the source signal line driver circuit 915. Then, in addition to connecting the source signal line 912 to the source signal line driver circuit 915, the gate signal line 911 is connected to the writing gate signal line driver circuit 913. Then, a signal is input selectively to the m-th gate signal line 911 from the writing gate signal line driver circuit 913 to turn on the first transistor 901, and signals for writing are input to the first to last source signal lines 912 from the source signal line driver circuit 915. This signal makes the m-th light-emitting element 903 is made to be in an emitting or non-emitting state.

Immediately after the writing period for the m-th row is completed as described above, an erasing period for the (n+1)-th row is started. For that purpose, the gate signal line 911 and the writing gate signal line driver circuit 913 are made to be unconnected to each other, and the switch 920 is switched to connect the source signal line 912 and the power source 916. Further, the gate signal line 911, which is unconnected to the writing gate signal line driver circuit 913, is made to be connected to the erasing gate signal line driver circuit 914. Then, a signal is input selectively to the (n+1)-th gate signal line 911 from the erasing gate signal line driver circuit 914 to turn on the first transistor 901, and an erasing signal is input from the power source 916. Immediately after the erasing period for the (n+1)-th row is completed, a writing period for the (m+1)-th row is started. Then, an erasing period and a writing period may be repeated in the same way until an erasing period for the last row is completed.

Although the example in which the writing period for the m-th row is provided between the erasing period for the n-th row and the erasing period for the (n+1)-th row is described in the present embodiment mode, the present invention is not limited to this. The writing period for the m-th row may be provided between an erasing period for (n−1)-th row and an erasing period for n-th row.

In addition, in the present embodiment mode, the operation in which the erasing gate signal line driver circuit 914 and one gate signal line 911 are made to be unconnected to each other and the writing gate signal line driver circuit 913 and the other gate signal line 911 are made to be connected to each other is repeated as the non-emission period 504d is provided in the sub-frame 504. This type of operation may be performed in a sub-frame in which a non-emission period is not particularly provided.

Embodiment Mode 4

Examples of a cross-sectional view of a light-emitting device including a light-emitting element according to the present invention will be described with reference to FIGS. 7A to 7C.

Figure 7A:
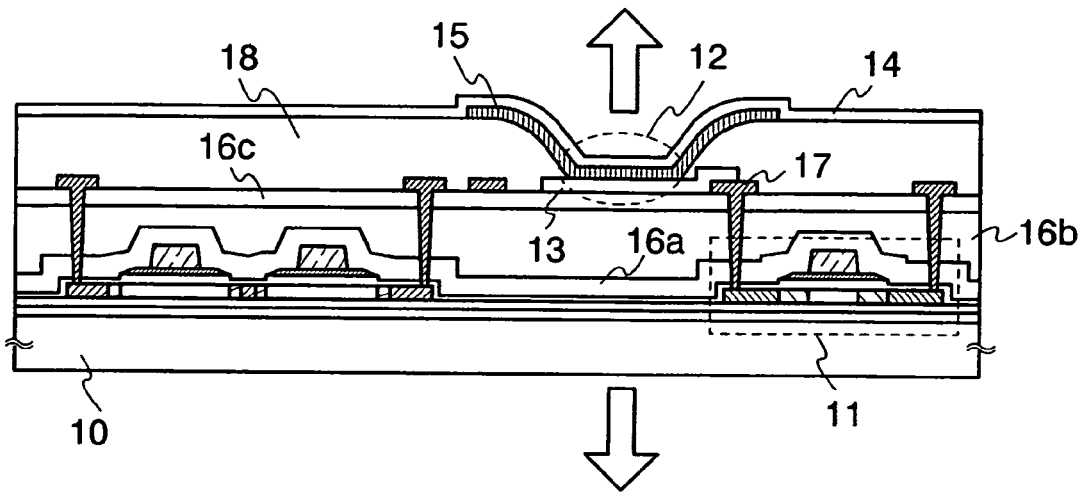
FIGS. 7A to 7C are cross-sectional views of light-emitting devices to which the present invention is applied.
Figure 7B:
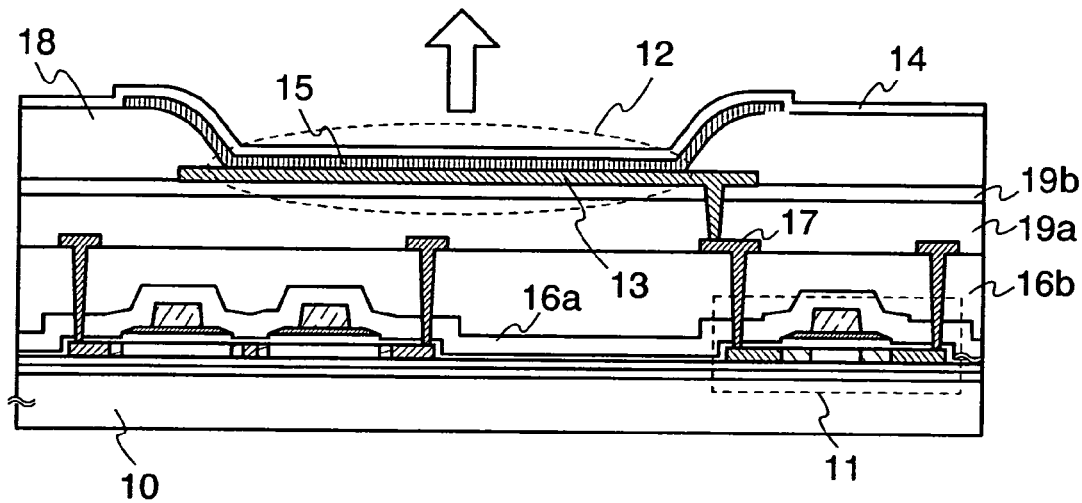
Figure 7C:
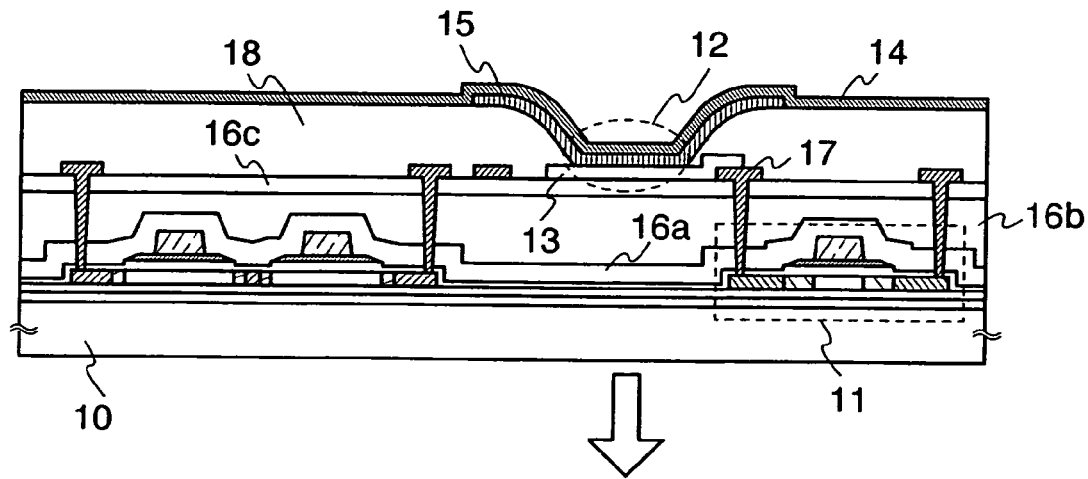

In each of FIGS. 7A to 7C, a portion surrounded by a dotted line is a transistor 11 provided for driving a light-emitting element 12 according to the present invention. The light-emitting element 12 is a light-emitting element according to the present invention, which has a light-emitting layer 15 between a first electrode 13 and a second electrode 14. In the light-emitting layer 15, a layer including a phenathroline derivative according to the present invention is provided. The first electrode 13 and a drain of the transistor 11 are electrically connected to each other by a wiring 17 running through a first interlayer insulating film 16 (16a to 16c). In addition, the light-emitting element 12 is separated by a partition layer 18 from another light-emitting element provided adjacently. A light-emitting device that has this structure according to the present invention is provided over substrate 10.

The transistor 11 shown in each of FIGS. 7A to 7C is a top-gate TFT in which a gate electrode is provided on the opposite side of a semiconductor layer as a center from a substrate. However, the structure of the transistor 11 is not particularly limited. For example, a bottom-gate TFT may be used. In the case of a bottom-gate TFT, a TFT where a protective film is formed on a semiconductor layer that forms a channel (a channel-protection TFT) may be used, or a TFT where a portion of a semiconductor layer that forms a channel is concave (a channel-etch TFT) may be used.

In addition, a semiconductor layer forming the transistor 11 may be either crystalline or amorphous, or alternatively, may be semi-amorphous.

The following will describe a semi-amorphous semiconductor. The semi-amorphous semiconductor is a semiconductor that has an intermediate structure between amorphous and crystalline (such as single-crystal or polycrystalline) structures and has a third state that is stable in terms of free energy, which includes a crystalline region that has short range order and lattice distortion. Further, a crystal grain from 0.5 to 20 nm is included in at least a region in a film of the semi-amorphous semiconductor. A raman spectrum of the semi-amorphous semiconductor has a shift to a lower wavenumber side than 520 cm$^{-1}$. In X-ray diffraction, diffraction peaks of (111) and (220) due to a Si crystal lattice are observed. Hydrogen or halogen is included at 1 atomic % or more in the semi-amorphous semiconductor to terminate a dangling bond. Therefore, the semi-amorphous semiconductor is also referred to as a micro-crystalline semiconductor. A suicide gas is decomposed by glow discharge (plasma CVD) to form the semi-amorphous semiconductor. As the suicide gas, in addition to $SiH_4$, a gas such as $Si_2H_6$, $SiH_2Cl_2$, $SiHCl_3$, $SiCl_4$, or $SiF_4$ can be used. This suicide gas may be diluted with $H_2$ or with $H_2$ and one kind or plural kinds of rare gas elements selected from He, Ar, Kr, and Ne, where the dilution ratio is in the range of 2:1 to 1000:1. The pressure during glow discharge is approximately in the range of 0.1 Pa to 133 Pa, and the power supply frequency is in the range of 1 MHz to 120 MHz, preferably 13 MHz to 60 MHz. The substrate heating temperature may be 300° C. or less, preferably 100 to 250° C. It is desirable to control an impurity of an atmospheric constituent such as oxygen, nitrogen, or carbon to have a concentration of $1\times10^{20}/cm^3$ or less as an impurity element in the film, in particular, the oxygen concentration is controlled to be $5\times10^{19}/cm^3$ or less, preferably $1\times10^{19}/cm^3$ or less.

Further, specific examples of crystalline semiconductors for the semiconductor layer include single-crystal or polycrystalline silicon and silicon-germanium, which may be formed by laser crystallization or may be formed by crystallization with solid-phase growth using an element such as nickel.

In the case of using an amorphous material, for example, amorphous silicon to form the semiconductor layer, it is preferable that the light-emitting device have a circuit in which the transistor 11 and the other transistor (a transistor forming the circuit for driving the light-emitting element) are all n-channel transistors. Other than that case, the light-emitting device may have a circuit including one of an n-channel transistor and a p-channel transistor or may have a circuit including both an n-channel transistor and a p-channel transistor.

Further, the first interlayer insulating film 16 may be a multilayer as shown in FIGS. 7A and 7C, or may be a single layer. The first interlayer insulating film 16a includes an inorganic material such as silicon oxide or silicon nitride, and the first interlayer insulating film 16b includes a material with self-flatness such as acrylic, siloxane, or silicon oxide that can be used in coating deposition. In addition, the first interlayer insulating film 16c has a silicon nitride film including argon (Ar). The materials included in the respective layers are not particularly limited, and therefore materials other than the materials mentioned here may be used. Further, a layer including a material other than these materials may be combined. In this way, both of an inorganic material and an organic material, or one of an inorganic material and an organic material may be used to form the first interlayer insulating film 16.

As for the partition layer 18, it is preferable that an edge portion have a shape varying continuously in curvature radius. In addition, a material such as acrylic, siloxane, resist, or silicon oxide is used to form the partition layer 18. One or both of an inorganic material and an organic material may be used to form the partition layer 18.

In each of FIGS. 7A and 7C, only the first interlayer insulating film 16 is provided between the transistor 11 and the light-emitting element 12. However, as shown in FIG. 7B, a second interlayer insulating film 19 (19a and 19b) may be provided in addition to the first interlayer insulating film 16 (16a and 16b). In the light-emitting device shown in FIG. 7B, the first electrode 13 is connected to the wiring 17 through the second interlayer insulating film 19.

The second interlayer insulating film 19 may be a multi-layer or a single layer in the same way as the first interlayer insulating film 16. The second interlayer insulating film 19a includes a material with self-flatness such as acrylic, siloxane (a compound that has a framework structure formed by a bond between silicon (Si) and oxygen (O) and includes an organic group such as an alkyl group as a substituent), silicon oxide that can be used in coating deposition. In addition, the second interlayer insulating film 19b has a silicon nitride film including argon (Ar). The materials included in the respective layers are not particularly limited, and therefore materials other than the materials mentioned here may be used. Further, a layer including a material other than these materials may be combined. In this way, both of an inorganic material and an organic material, or one of an inorganic material and an organic material may be used to form the second interlayer insulating film 19.

In the light-emitting element 12, in the case where both of the first electrode 13 and the second electrode 14 are formed by using a light-transmitting material, emitted light can be extracted from both the first electrode 13 side and the second electrode 14 side as indicated by outline arrows of FIG. 7A. In the case where only the second electrode 14 is formed by using a light-transmitting material, emitted light can be extracted from only the second electrode 14 side as indicated by an outline arrow of FIG. 7B. In this case, it is preferable that the first electrode 13 include a highly reflective material or that a film composed of a highly reflective material (a reflective film) be provided below the first electrode 13. In the case where only the first electrode 13 is formed by using a light-transmitting material, emitted light can be extracted from only the first electrode 13 side as indicated by an outline arrow of FIG. 7C. In this case, it is preferable that the second electrode 14 include a highly reflective material or that a reflective film is provided above the second electrode 14.

In addition, in the case of the light-emitting element 12, the first electrode 13 may function as an anode while the second electrode 14 functions as a cathode, or alternatively, the first electrode 13 may function as a cathode while the second electrode 14 functions as an anode. However, the transistor 11 is a p-channel transistor in the former case, and the transistor 11 is an n-channel transistor in the latter case.

As described above, in the present embodiment mode, an active light-emitting device in which driving of a light-emitting element is controlled by a transistor is described. However, in addition to this active light-emitting device, a passive light-emitting device in which a light-emitting element is driven without especially providing an element for driving such as a transistor may be used. The passive light-emitting device also can be driven with low power consumption by including a light-emitting element according to the present invention that operates at a low driving voltage.

Embodiment Mode 5

By mounting a light-emitting device according to the present invention, an electronic device that is capable of operating at a low driving voltage can be obtained.

Figure 8A:
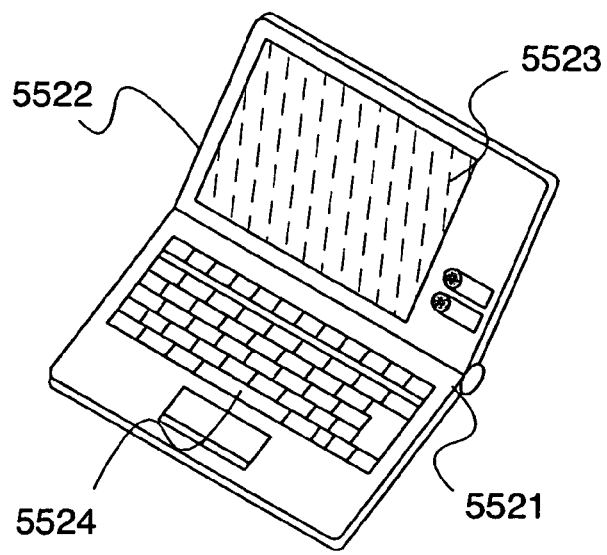
FIGS. 8A to 8C are diagrams of electronic devices to which the present invention is applied.
Figure 8B:
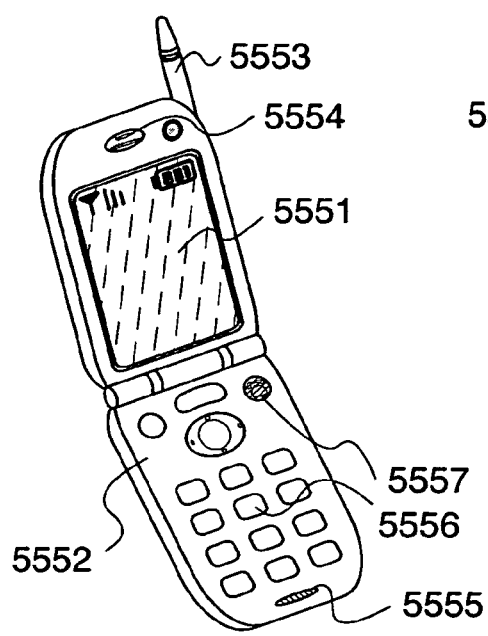
Figure 8C:
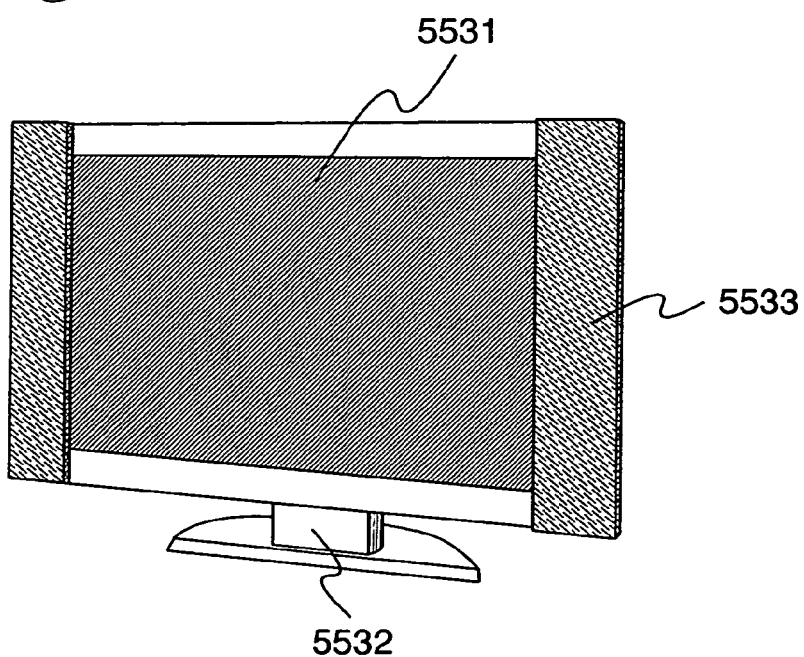

FIGS. 8A to 8C show examples of an electronic device mounted with a light-emitting device to which the present invention is applied.

FIG. 8A shows a laptop personal computer manufactured according to the present invention, which includes a main body 5521, a frame body 5522, a display portion 5523, and a keyboard 5524. The personal computer can be completed by incorporating a light-emitting device that has a light-emitting element according to the present invention into the display portion 5523.

FIG. 8B shows a cellular phone manufactured according to the present invention, which includes a main body 5552, a display portion 5551, a voice output portion 5554, a voice input portion 5555, operation keys 5556 and 5557, and an antenna 5553. The cellular phone can be completed by incorporating a light-emitting device that has a light-emitting element according to the present invention into the display portion 5551.

FIG. 8C shows a television manufactured according to the present invention, which includes a display portion 5531, a frame body 5532, and a speaker 5533. The television can be completed by incorporating a light-emitting device that has a light-emitting element according to the present invention into the display portion 5531.

As described above, a light-emitting device according to the present invention is suitable for use as display portions of various electronic devices.

Further, in addition to the electronic device described above, a light-emitting device that has a light-emitting element according to the present invention may be mounted in devices such as a navigation system and a lighting apparatus.

Embodiment 1

Synthesis Example 1

Here is a synthesis method of a compound represented by the structure formula (9), 5,6-dihydro-4,7-dimethyl-dibenzo[b,j]-1,10-phenanthroline.

The catalyst quantity (approximately 5 mol %) of p-toluenesulfonic acid monohydrate was added to an ethylenegly-col monoethyl ether (100 mL) solution of 2'-aminoacetophenon (24.6 g, 182 mmol) and 1,2-cyclohexadione (10.2 g, 91 mmol), and reflux was performed on heating for 48 hours (Synthesis Scheme b-1). The reaction solution was cooled to room temperature, and a precipitated solid was filtered. The filtrate was recrystallized with tetrahydrofran to obtain a compound at a yield of 38%. Measurement of the obtained compound by NMR could confirm that the obtained compound was 5,6-dihydro-4,7-dimethyl-dibenzo[b, j]-1,10-phenanthroline.

Here is NMR data of the obtained compound.

$^1$H NMR (300 MHz, CDCl$_3$) δ 8.43 (d, 2H, J=8.4 Hz), 7.97 (d, 2H, J=8.0 Hz), 7.66 (dd, 2H, J=8.4, 15 Hz), 7.53 (dd, 2H, J=8.0, 15 Hz), 3.19 (s, 4H), 2.67 (s, 6H)

Further, the obtained compound was deposited by evaporation, and measurement by a photoelectron spectrometer (AC-2 from Riken Keiki Co., Ltd.) was performed to find that the ionization potential of the thin-film compound was −5.26 eV. In addition, an absorption spectrum of the thin-film compound was measured by an ultraviolet-visible spectrophotometer (V-550 from JASCO Corporation), and the wavelength of an absorption edge on the longer wavelength side of the absorption spectrum was made an energy gap (3.09 eV) to find that the LUMO level of the compound was −2.17 eV.

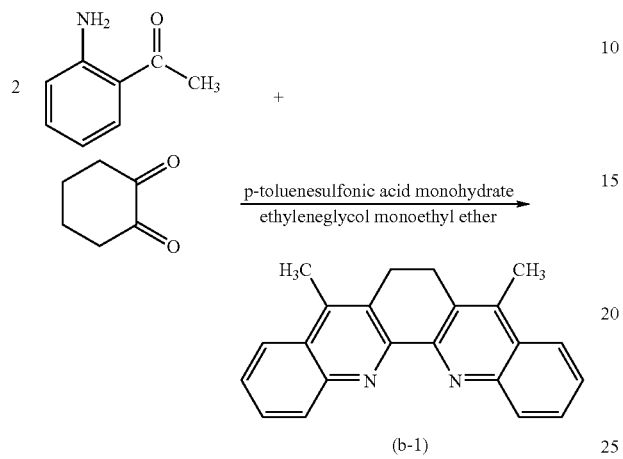

(b-1)

Synthesis Example 2

Here is a synthesis method of a compound represented by the structure formula (10), 5,6-dihydro-4,7-diphenyl-dibenzo[b,j]-1,10-phenanthroline.

To an ethyleneglycol monoethyl ether (100 mL) solution of 2'-aminobenzophenon (19.3 g, 98 mmol) and 1,2-cyclohexadion (5.0 g, 45 mmol), p-toluenesulfonic acid monohydrate (890 mg, 4.7 mmol) was added, and reflux was performed on heating for 24 hours. The reaction solution was cooled to room temperature, and a precipitated crystal was obtained by filtering (Synthesis Scheme c-1). The obtained crystal was recrystallized with chloroform to obtain a compound at a yield of 52%. Measurement of the obtained compound by NMR could confirm that the obtained compound was 5,6-dihydro-4,7-diphenyl-dibenzo[b, j]-1,10-phenanthroline.

Here is NMR data of the obtained compound.

$^1$H NMR (300 MHz, CDCl$_3$) δ 8.53 (d, 2H, J=8.4 Hz), 7.70 (ddd, 2H, J=2.0, 6.3, 10.5 Hz), 7.38-7.56 (m, 10H), 7.31 (dd, 4H, J=2.0, 8.4 Hz), 2.84 (s, 4H)

Further, the obtained compound was deposited by evaporation, and measurement by a photoelectron spectrometer (AC-2 from Riken Keiki Co., Ltd.) was performed to find that the ionization potential of the thin-film compound was −5.32 eV. In addition, an absorption spectrum of the thin-film compound was measured by an ultraviolet-visible spectrophotometer (V-550 from JASCO Corporation), and the wavelength of an absorption edge on the longer wavelength side of the absorption spectrum was made an energy gap (3.22 eV) to find that the LUMO level of the compound was −2.10 eV.

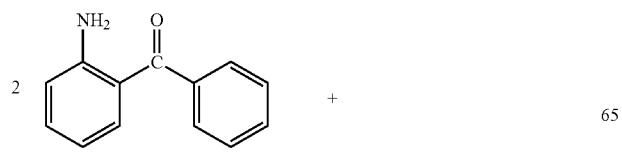

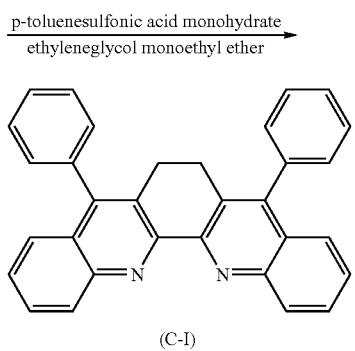

(C-I)

Synthesis Example 3

Here is a synthesis method of a compound represented by the structure formula (4), 5,6-dihydro-4,7-di[2-(3-fluoro)phenylethenyl]-dibenzo[b,j]-1,10-phenanthroline.

An acetic anhydride (approximately 50 mL) solution of a compound represented by the structure formula (9), 5,6-dihydro-4,7-dimethyl-dibenzo[b, j]-1,10-phenanthroline (7.7 g, 25 mmol), and 3-fluorobenzaldehyde (9.2 g, 74 mmol) was held at reflux on heating for 36 hours (Synthesis Scheme d-1). The reaction solution was made basic with a 10% sodium hydroxide solution, and then, extraction with ethyl acetate was performed. The organic layer was dried with magnesium sulfate, filtered, and condensed, and the residue was twice purified by alumina chromatography (developing solvent: methylene chloride) to obtain a compound. Then, the obtained compound was further purified by liquid preparative chromatography (from Japan Analytical Industry Co., Ltd., recycling preparative HPLC, LC-908W-C60, developing solvent: chloroform), and then, recrystallization was performed with a hexane/ethyl acetate mixed solution to obtain a compound at yield of 15%. Measurement of the obtained compound by NMR could confirm that the obtained compound was 5,6-dihydro-4,7-di[2-(3-fluoro)phenylethenyl]-dibenzo[b,j]-1,10-phenanthroline.

Here is NMR data of the obtained compound.

$^1$U NMR (300 MHz, CDCl) δ 8.49 (d, 2H, J=8.7 Hz), 6.08 (d, 2H, J=8.4 Hz), 7.26-7.80 (m, 12H), 7.07 (dd, 2H, J=7.2, 17.0 Hz), 6.83 (d, 2H, J=17.0 Hz), 3.28 (s, 4H)

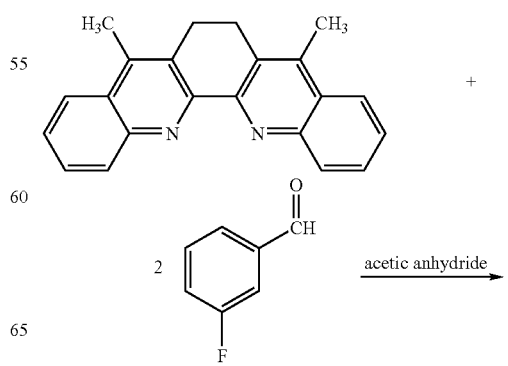

-continued

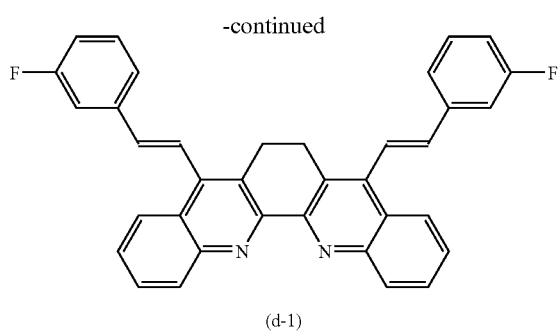

(d-1)

Embodiment 2

Figure 2:
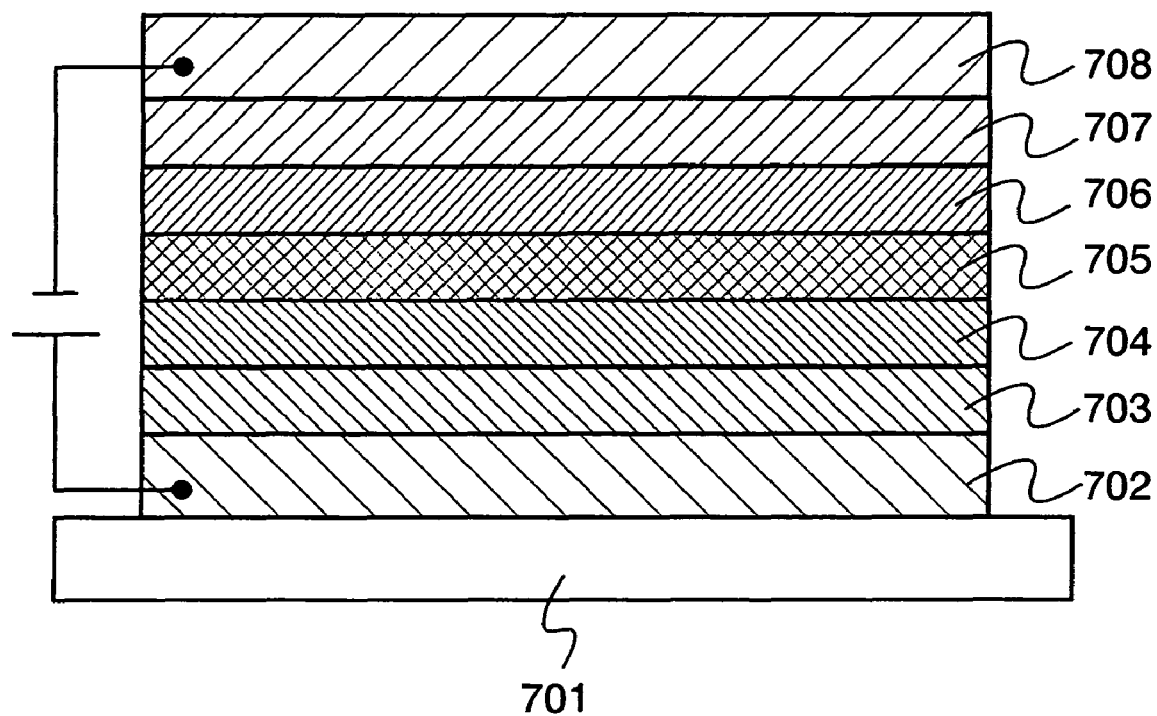
FIG. 2 is a diagram for describing a method of manufacturing a light-emitting element according to the present invention.

A light-emitting element manufactured with the use of a compound represented by the structure formula (9) will be described with reference to FIG. 2.

Indium tin oxide containing silicon was deposited on a substrate 701 by sputtering to form a first electrode 702, where the film thickness of the first electrode 702 was made to be 110 nm, and a substrate composed of glass was used as the substrate 701.

Next, 4,4'-bis[N-{4-(N,N-di-m-tolylamino)phenyl}-N-phenylamino]biphenyl (abbreviation: DNTPD) was deposited on the first electrode 702 by vacuum evaporation to form a first layer 703 composed of DNTPD, where the film thickness of the first layer 703 was made to be 50 nm.

Next, 4,4'-bis[N-(I-naphthyl)-N-phenyl-amino]-biphenyl (abbreviation: α-NPD) was deposited on the first layer 703 by vacuum evaporation to form a second layer 704 composed of α-NPD, where the film thickness of the second layer 704 was made to be 10 nm.

Next, tris(8-quinolinolato) aluminum (abbreviation: $Alq_3$) and coumarin 6 were deposited on the second layer 704 by co-evaporation to form a third layer 705 including $Alq_3$ and coumarin 6, where the weight ratio of $Alq_3$ to coumarin 6 was controlled to be 1:0.003. This makes coumarin 6 dispersed in $Alq_3$. In addition, the film thickness of the third layer 705 was made to be 37.5 nm. It is to be noted that co-evaporation is an evaporation method in which evaporation is performed simultaneously from a plurality of evaporation sources.

Next, $Alq_3$ was deposited on the third layer 705 by vacuum evaporation to form a fourth layer 706 composed of $Alq_3$, where film thickness of the fourth layer 706 was made to be 20 nm.

Next, a compound represented by the structure formula (9) and lithium were deposited on the fourth layer 706 by co-evaporation to form a fifth layer 707 including the compound represented by the structure formula (9) and lithium, where the weight ratio of the compound represented by the structure formula (9) to lithium was controlled to be 1:0.01. This makes lithium dispersed in the compound represented by the structure formula (9). In addition, the film thickness of the fifth layer 707 was made to be 20 nm.

Next, aluminum was deposited on the fifth layer 707 by vacuum evaporation to form a second electrode 708. The film thickness of the second electrode 708 was made to be 100 nm.

In the thus manufactured light-emitting element, when a voltage is applied to the first electrode 702 and the second electrode 708 to flow current, coumarin 6 produces luminescence. In this case, the first electrode 702 serves as an anode and the second electrode 708 serves as a cathode. In addition, the first layer 703, the second layer 704, the third layer 705, the fourth layer 706, and the fifth layer 707 serve as a hole injecting layer, a hole transporting layer, a light-emitting layer, an electron transporting layer, and an electron injecting layer, respectively.

Figure 9:
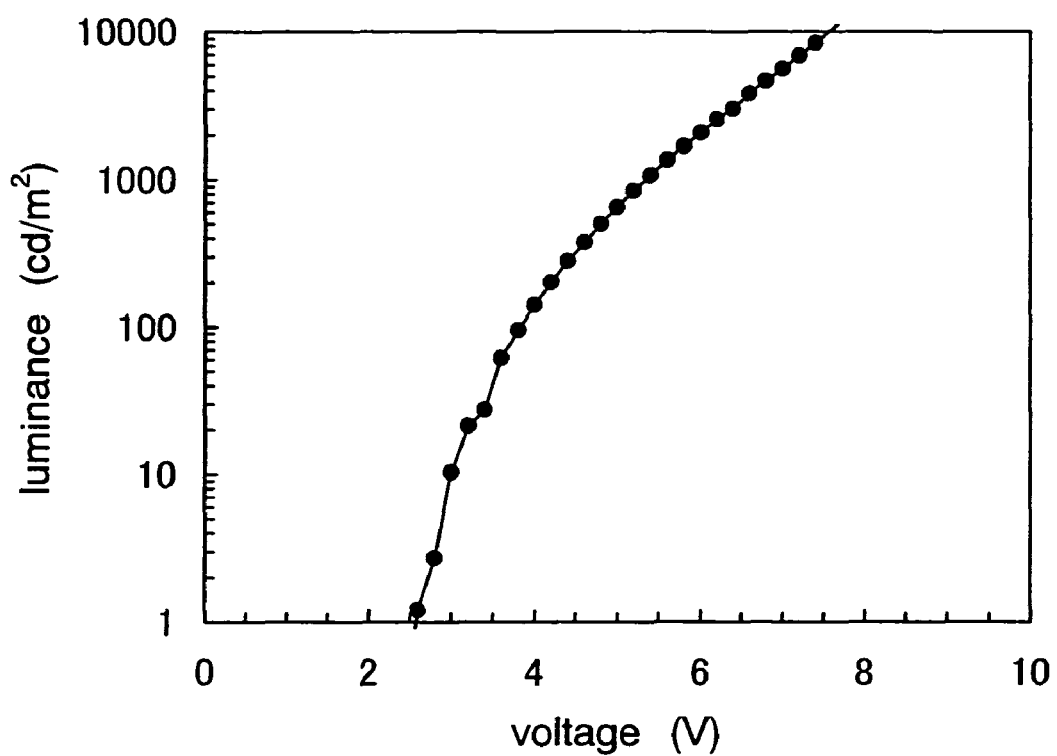
FIG. 9 is a diagram showing voltage-luminance characteristics of a light-emitting element according to the present invention.
Figure 10:
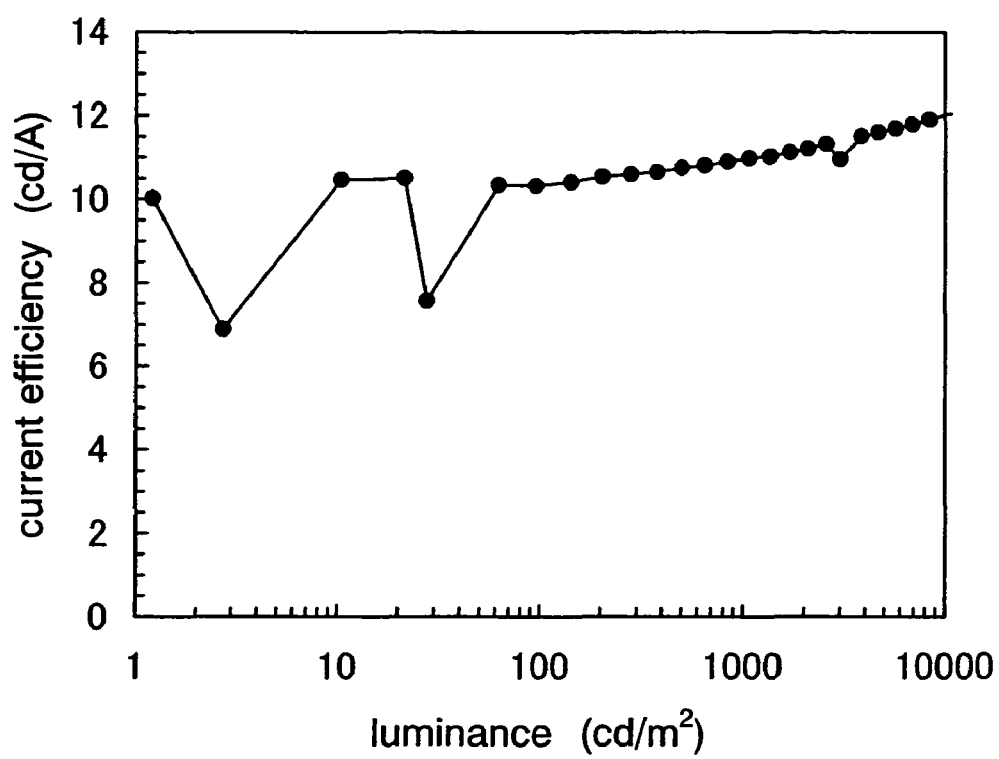
FIG. 10 is a diagram showing luminance-current efficiency characteristics of a light-emitting element according to the present invention.

FIGS. 9 and 10 show voltage-luminance characteristics and luminance-current efficiency characteristics of the light-emitting element in the present embodiment, respectively. In FIG. 9, the horizontal axis indicates a voltage, and the vertical axis indicates a luminance. In addition, in FIG. 10, the horizontal axis indicates a luminance, and the vertical axis indicates a current efficiency. From FIG. 10, it is determined that the light-emitting element in the present embodiment provides a current efficiency of approximately 11 cd/A at a luminance of 1000 cd/m$^2$ and is thus a light-emitting element that is excellent in current efficiency. In addition, the light-emitting element exhibits CIE chromaticity coordinates of luminescence of (x, y)=(0.29, 0.63).

As can be seen from the results described above, luminescence derived from coumarin 6 can be obtained well from the light-emitting element in the present embodiment, and the light-emitting element is excellent in current efficiency. It is believed that this is because the layer including the compound represented by the structure formula (9) and lithium (Li) functions well as an electron injecting layer.

Embodiment 3

A light-emitting element manufactured with the use of a compound represented by the structure formula (10) will be described. It is to be noted that FIG. 2 is used for description since the light-emitting element in the present embodiment has the same structure including five layers between a first electrode and a second electrode as the light-emitting element in Embodiment 2.

Indium tin oxide containing silicon was deposited on a substrate 701 by sputtering to form a first electrode 702, where the film thickness of the first electrode 702 was made to be 110 nm, and a substrate composed of glass was used as the substrate 701.

Next, 4,4'-bis[N-{4-(N,N-di-m-tolylamino) phenyl}-N-phenylamino]biphenyl (abbreviation: DNTPD) was deposited on the first electrode 702 by vacuum evaporation to form a first layer 703 composed of DNTPD, where the film thickness of the first layer 703 was made to be 50 nm.

Next, 4,4'-bis[N-(I-naphthyl)-N-phenyl-amino]-biphenyl (abbreviation: α-NPD) was deposited on the first layer 703 by vacuum evaporation to form a second layer 704 composed of α-NPD, where the film thickness of the second layer 704 was made to be 10 nm.

Next, tris(8-quinolinolato) aluminum (abbreviation: $Alq_3$) and coumarin 6 were deposited on the second layer 704 by co-evaporation to form a third layer 705 including $Alq_3$ and coumarin 6, where the weight ratio of $Alq_3$ to coumarin 6 was controlled to be 1:0.003. This makes coumarin 6 dispersed in $Alq_3$. In addition, the film thickness of the third layer 705 was made to be 37.5 nm.

Next, $Alq_3$ was deposited on the third layer 705 by vacuum evaporation to form a fourth layer 706 composed of $Alq_3$, where film thickness of the fourth layer 706 was made to be 20 nm.

Next, a compound represented by the structure formula (10) and lithium were deposited on the fourth layer 706 by co-evaporation to form a fifth layer 707 including the compound represented by the structure formula (10) and lithium, where the weight ratio of the compound represented by the structure formula (10) to lithium was controlled to be 1:0.01. This makes lithium dispersed in the compound represented by the structure formula (10). In addition, the film thickness of the fifth layer 707 was made to be 20 nm.

Next, aluminum was deposited on the fifth layer 707 by vacuum evaporation to form a second electrode 708.

As described above, the light-emitting element in the present embodiment is different in substance included in the fifth layer 707 from the light-emitting element in Embodiment 2. However, the rest of the light-emitting element in the present embodiment is manufactured to have the same structure as the light-emitting element in Embodiment 2.

In the thus manufactured light-emitting element, when a voltage is applied to the first electrode 702 and the second electrode 708 to flow current, coumarin 6 produces luminescence. In this case, the first electrode 702 serves as an anode and the second electrode 708 serves as a cathode. In addition, the first layer 703 composed of DNTPD, the second layer 704 composed of cc-NPD, the third layer 705 including $Alq_3$ and coumarin 6, the fourth layer 706 composed of $Alq_3$, and the fifth layer 707 including the compound represented by the structure formula (10) and lithium (Li) serve as a hole injecting layer, a hole transporting layer, a light-emitting layer, an electron transporting layer, and an electron injecting layer, respectively.

Figure 11:
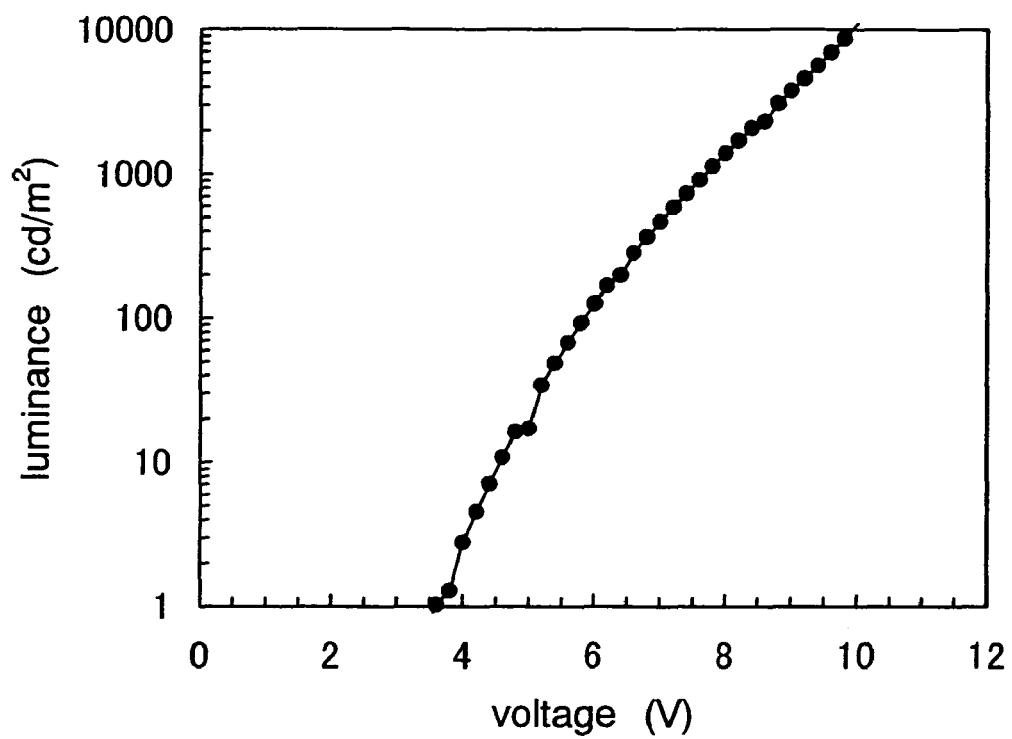
FIG. 11 is a diagram showing voltage-luminance characteristics of a light-emitting element according to the present invention.
Figure 12:
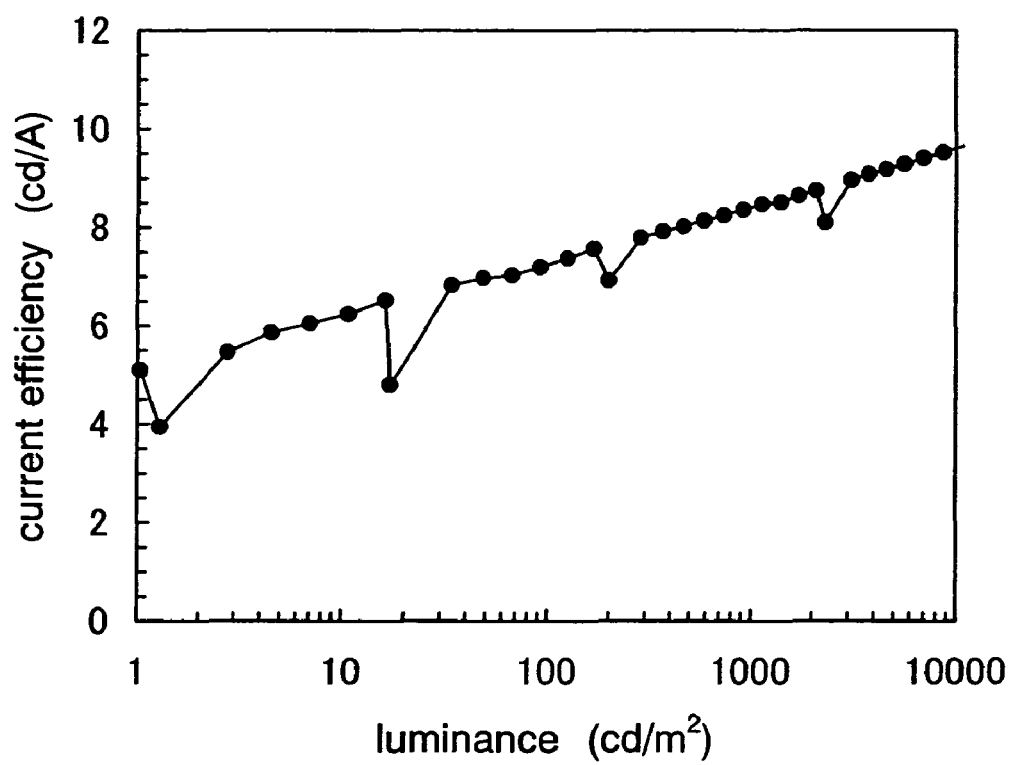
FIG. 12 is diagram showing luminance-current efficiency characteristics of a light-emitting element according to the present invention.

FIGS. 11 and 12 show voltage-luminance characteristics and luminance-current efficiency characteristics of the light-emitting element in the present embodiment, respectively. In FIG. 11, the horizontal axis indicates a voltage, and the vertical axis indicates a luminance. In addition, in FIG. 12, the horizontal axis indicates a luminance, and the vertical axis indicates a current efficiency. From FIGS. 11 and 12, it is determined that the light-emitting element in the present embodiment provides a current efficiency of approximately 8.5 cd/A at a luminance of 1000 $cd/m^2$ and is thus a light-emitting element that is excellent in current efficiency, and that the light-emitting element in the present embodiment emits light with a high luminance of 10000 $cd/m^2$ when a voltage of 10 V is applied. In addition, the light-emitting element exhibits CIE chromaticity coordinates of luminescence of (x, y)=(0.29, 0.62).

As can be seen from the results described above, luminescence derived from coumarin 6 can be obtained well from the light-emitting element in the present embodiment, and the light-emitting element is excellent in current efficiency. It is believed that this is because the layer including the compound represented by the structure formula (10) and lithium (Li) functions well as an electron injecting layer.

Although the present invention has been fully described by way of example with reference to the accompanying drawings, it is to be understood that various changes and modifications will be apparent to those skilled in the art. Therefore, unless such changes and modifications depart from the scope of the present invention hereinafter defined, they should be construed as being included therein.

This application is based on Japanese Patent Application serial no. 2004-200059 filed in Japan Patent Office on Jul. 7, 2004, the entire contents of which are hereby incorporated by reference.

What is claimed is:

1. A phenanthroline derivative represented by a general formula (1),

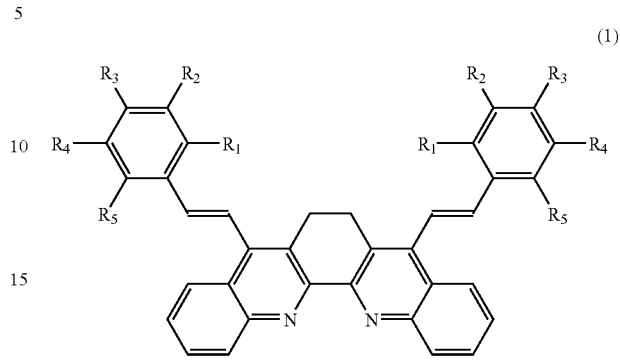

wherein each of $R_1$ to $R_5$ is selected from the group consisting of a hydrogen atom, an alkyl group having 1 to 4 carbon atoms and a halogen group.

2. A light-emitting element comprising the phenanthroline derivative according to claim 1 and at least one element selected from alkali metals and alkali-earth metals.

3. A light-emitting element comprising a layer in which a phenanthroline derivative represented by a general formula (3) and at least one element selected from alkali metals and alkali-earth metals are mixed,

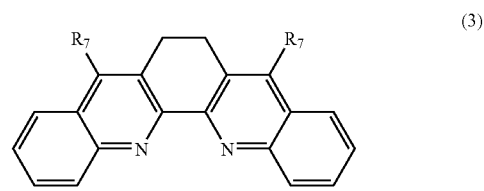

wherein $R_7$ is selected from the group consisting of an alkyl group having 1 to 4 carbon atoms, an alkenyl group having 1 to 4 carbon atoms, and an aryl group having 6 to 10 carbon atoms.

4. A light-emitting device comprising the light-emitting element according to claim 2.

5. A light-emitting device that has a display function, comprising a pixel portion in which a circuit including the light-emitting element according to claim 2 is arranged.

6. An electronic device using the light-emitting device according to claim 4 for a display portion.

7. An electronic device using the light-emitting device according to claim 5 for a display portion.

8. A light-emitting device comprising the light-emitting element according to claim 3.

9. A light-emitting device that has a display function, comprising a pixel portion in which a circuit including the light-emitting element according to claim 3 is arranged.

10. A light-emitting device according to claim 3, wherein the layer is an electron injecting layer.

* * * * *

UNITED STATES PATENT AND TRADEMARK OFFICE
CERTIFICATE OF CORRECTION

PATENT NO. : 7,750,159 B2
APPLICATION NO. : 10/579114
DATED : July 6, 2010
INVENTOR(S) : Ryoji Nomura and Daisuke Kumaki It is certified that error appears in the above-identified patent and that said Letters Patent is hereby corrected as shown below:

In the Specification:

Column 7, line 60; Change "111 Can be" to --111 can be--.
Column 14, line 22; Change "A suicide" to --A silicide--.
Column 19, line 31; Change "[N-I-naphthyl)" to --[N-1-naphthyl)--.
Column 20, line 45; Change "[N-I-naphthyl)" to --[N-1-naphthyl)--.

Signed and Sealed this
Nineteenth Day of November, 2013

Teresa Stanek Rea
*Deputy Director of the United States Patent and Trademark Office*